(12) United States Patent
Babaev

(10) Patent No.: US 7,572,268 B2
(45) Date of Patent: Aug. 11, 2009

(54) APPARATUS AND METHODS FOR THE SELECTIVE REMOVAL OF TISSUE USING COMBINATIONS OF ULTRASONIC ENERGY AND CRYOGENIC ENERGY

(75) Inventor: Eilaz P. Babaev, Minnetonka, MN (US)

(73) Assignee: Bacoustics, LLC, Minnetonka, MN (US)

( * ) Notice: Subject to any disclaimer, the term of this patent is extended or adjusted under 35 U.S.C. 154(b) by 0 days.

(21) Appl. No.: 11/250,870

(22) Filed: Oct. 13, 2005

(65) Prior Publication Data

US 2007/0088217 A1    Apr. 19, 2007

(51) Int. Cl.
*A61B 17/32* (2006.01)
*A61B 18/18* (2006.01)

(52) U.S. Cl. .................................... 606/169; 606/20
(58) Field of Classification Search ......... 606/169–170, 606/20
See application file for complete search history.

(56) References Cited

U.S. PATENT DOCUMENTS

| | | | |
|---|---|---|---|
| 3,220,414 A | 11/1965 | Johnston | |
| 3,237,623 A | 3/1966 | Gordon | |
| 3,589,363 A | 6/1971 | Banko et al. | |
| 3,889,680 A | 6/1975 | Armao | |
| 4,015,606 A | 4/1977 | Mitchiner et al. | |
| 4,082,096 A | 4/1978 | Benson | |
| 4,528,979 A * | 7/1985 | Marchenko et al. | 606/21 |
| 4,724,834 A | 2/1988 | Alperovich et al. | |
| 4,823,790 A * | 4/1989 | Alperovich et al. | 606/24 |
| 4,832,022 A * | 5/1989 | Tjulkov et al. | 606/22 |
| 4,946,460 A | 8/1990 | Merry et al. | |
| 5,078,713 A | 1/1992 | Varney | |
| 5,108,390 A | 4/1992 | Potocky | |
| 5,139,496 A | 8/1992 | Hed | |
| 5,242,449 A * | 9/1993 | Zaleski | 606/107 |
| 5,334,181 A | 8/1994 | Rubinsky et al. | |
| 5,433,717 A | 7/1995 | Rubinsky et al. | |
| 5,452,582 A | 9/1995 | Longsworth | |
| 5,520,682 A | 5/1996 | Baust et al. | |
| 5,649,936 A | 7/1997 | Real | |
| 5,716,353 A | 2/1998 | Matsuura et al. | |
| 5,899,898 A | 5/1999 | Arless et al. | |
| 5,899,899 A | 5/1999 | Arless | |
| 5,906,612 A | 5/1999 | Chinn | |
| 5,913,885 A | 6/1999 | Klatz et al. | |
| 5,916,242 A | 6/1999 | Schwartz | |
| 5,957,963 A | 9/1999 | Dobak, III | |

(Continued)

FOREIGN PATENT DOCUMENTS

WO    WO 01/76517    10/2001

OTHER PUBLICATIONS

Mark D. Andrews, Cryosurgery for Common Skin Conditions, American Family Physician, vol. 69 (10) / May 15, 2005, 2365-2372.

*Primary Examiner*—Todd E Manahan
*Assistant Examiner*—Diane Yabut

(57) ABSTRACT

An ultrasonic apparatus and method is provided for the selective and targeted removal of unwanted tissues. The apparatus and methods may utilize combinations of ultrasonic and cryogenic energy for the selective removal tissue. The apparatus generates and delivers to the tissue cryogenic and ultrasonic energy either in combination or in sequence, provides resize ablation of unwanted tissue parts, and may be used on various body tissues including internal organs.

14 Claims, 8 Drawing Sheets

U.S. PATENT DOCUMENTS

| | | | |
|---|---|---|---|
| 6,030,412 A | 2/2000 | Klatz et al. | |
| 6,039,730 A | 3/2000 | Rabin et al. | |
| 6,041,787 A | 3/2000 | Rubinsky | |
| 6,042,579 A | 3/2000 | Elsberry et al. | |
| 6,045,532 A | 4/2000 | Eggers et al. | |
| 6,051,019 A | 4/2000 | Dobak, III et al. | |
| 6,074,412 A | 6/2000 | Mikus | |
| 6,083,166 A | 7/2000 | Holdaway et al. | |
| 6,096,068 A | 8/2000 | Dobak, III et al. | |
| 6,106,518 A | 8/2000 | Wittenberger et al. | |
| 6,126,684 A | 10/2000 | Gobin et al. | |
| 6,149,677 A | 11/2000 | Dobak, III et al. | |
| 6,245,095 B1 | 6/2001 | Dobak, III et al. | |
| 6,248,126 B1 | 6/2001 | Lesser et al. | |
| 6,280,439 B1 * | 8/2001 | Martin et al. | 606/21 |
| 6,280,441 B1 | 8/2001 | Ryan | |
| 6,386,202 B1 | 5/2002 | Frazee | |
| 6,413,263 B1 | 7/2002 | Lobdill et al. | |
| 6,475,212 B2 | 11/2002 | Dobak et al. | |
| 6,546,932 B1 | 4/2003 | Nahon et al. | |
| 6,551,309 B1 * | 4/2003 | LePivert | 606/20 |
| 6,565,556 B1 | 5/2003 | Korpan et al. | |
| 6,582,368 B2 | 6/2003 | Holdaway et al. | |
| 6,648,880 B2 | 11/2003 | Chauvet et al. | |
| 6,663,554 B2 | 12/2003 | Babaev | |
| 6,786,902 B1 | 9/2004 | Rabin et al. | |
| 6,858,025 B2 | 2/2005 | Maurice | |
| 6,936,045 B2 | 8/2005 | Yu et al. | |
| 2002/0042609 A1 | 4/2002 | Kelman et al. | |

* cited by examiner

APPARATUS AND METHODS FOR THE SELECTIVE REMOVAL OF TISSUE USING COMBINATIONS OF ULTRASONIC ENERGY AND CRYOGENIC ENERGY

BACKGROUND OF THE INVENTION

1. Field of the Invention

The present invention relates to the removal of tissue from a patient, and more particularly, to apparatus and methods using combinations of ultrasonic and cryogenic energy to remove tissue.

2. Description of the Related Art

Human skin is the largest organ of the body and acts as an indicator reflecting various internal and external health related ailments. The skin protects the body from common physical, chemical, and microbiological invasion that humans are naturally exposed to in their everyday living environment.

Skin disorders are generally defined as diseases affecting the skin. Skin disorders frequently affect multiple layers of skin. Some common skin disorders include wrinkles, scars, warts, and non-metastatic melanomas, basilomas, human papilloma viruses, and various pre-cancerous and cancerous skin growths. Some skin disorders are local growths in the skin caused by viral infections, which are typically not contagious.

Typical methods for treating skin disorders include surgical removal, chemical peeling, and cryogenic and electrical treatments. These methods frequently have the disadvantages of destroying surrounding healthy tissue, increasing infection rates, high rates of recurrence, and/or substantial pain or discomfort following the procedure. Further, many existing methods are complicated and imprecise. This lack of precision in targeting the unhealthy tissue can result in a failure to fully remove the necessary harmful tissue, and also can result in damage to the surrounding healthy skin tissue. Any unhealthy tissue not removed can quickly become the basis for recurrence of the disorder. In addition, the treated tissue can become a point for introduction of infections or contaminants, because of the damage to or destruction of surrounding tissues. Therefore, a need exists for apparatus and methods, which target and completely or effectively completely remove diseased tissues without damage to the surrounding tissues.

SUMMARY OF THE INVENTION

The present invention is directed toward apparatus and methods for selective ablation of unwanted skin layers. Apparatus and methods in accordance with the present invention may meet the above-mentioned needs and also provide additional advantages and improvements that will be recognized by those skilled in the art upon review of the present disclosure.

An apparatus according to the present disclosure delivers ultrasonic and cryogenic energy to skin tissue either in combination or sequentially. Unwanted tissue layers may be destroyed and removed by this combined or sequential application of ultrasonic and cryogenic energy. The apparatus may be utilized for the treatment of diseased tissues or unwanted tissue layers/growths located either superficially or internally in human and animal bodies. The apparatus can be used for targeted and selective ablation of soft and hard tissues.

An embodiment of an apparatus in accordance with the present invention may be a hand-held device having a proximate end and a distal end. The proximate end may include a handle so that the device may be manipulated by a surgeon. An ultrasonic tip may be located on the distal end of the device. The ultrasonic tip can include a body, and the body may define one or more chambers. The ultrasonic tip may be cryogenically cooled by delivery of a cryogenic fluid from a reservoir into one or more chambers defined by the ultrasonic tip. An ultrasonic transducer may be used to excite the ultrasonic tip. Thus, the ultrasonic tip may be simultaneously cryogenically cooled and excited by the ultrasonic transducer or may be sequentially cooled and excited by the transducer so that simultaneous and sequential combinations of cryogenic and ultrasonic energy may be created at the ultrasonic tip. The ultrasonic tip may then be placed on tissue targeted for removal so as to deliver cryogenic energy and ultrasonic energy either in combination or in sequence to the tissue targeted for removal.

The cryogenic fluid will typically be in either a gas phase or liquid phase. A cryogenic gas or liquid may be used as would be recognized by those skilled in the art such as, for example, liquid nitrogen. The cryogenic fluid may be delivered to one or more of the chambers defined by the body of the ultrasonic tip. The cryogenic fluid may be delivered by one or more connecting tubes or other components designed to direct cryogenic fluid to flow into the chamber. In one possible embodiment, one or more inlet tubes are provided in communication with the chamber to introduce the cryogenic fluid into the chamber and one or more exit tubes are provided to permit the cryogenic fluid to be removed from the chamber or to flow through the chamber. In another possible embodiment, the interior chamber may be designed to approach the distal end of the ultrasonic tip to more efficiently cool the distal end.

The ultrasonic tip has an ultrasonically active distal end for delivering ultrasonic energy to the targeted tissue. This may be applied to the tissue in combination with, subsequent to, or prior to the application of cryogenic energy. The energy may be applied through direct contact, through an ice ball formed on the ultrasonic tip, or through cryogenic spray emitted from the ultrasonic tip. "Ice ball" as used herein, generally refers to the creation of ice particles or pieces, and not as the term is typically used in reference to cryogenic therapy. Although the particles or pieces of ice, herein labeled as an "ice ball," may have a rounded geometrical form, the particles or pieces of ice making up the "ice ball" do not necessarily have to be in the geometric form of a ball as will be recognized by those skilled in the art.

The ultrasonic tip is usually composed of a metal such as titanium, although the ultrasonic tip may also be composed of plastic or combinations of metal and plastic as would be recognized by those skilled in the art. An ultrasonic transducer may be used to excite the ultrasonic tip. The ultrasonic tip may be connected to the ultrasonic transducer by an ultrasonic horn. The ultrasonic tip may be detachable from the ultrasonic horn or permanently attached to the ultrasonic horn. A detachable ultrasonic tip may be disposable.

In other possible embodiments, the distal end of the ultrasonic tip may have various geometric shapes such as sharp-edged, conical, toothed, waved, flat, rounded, or a combination of shapes. The various shapes can be chosen as is appropriate for various procedures to be performed on the tissue. A detachable ultrasonic tip can allow a surgeon to vary the geometric shape of the distal end as is appropriate during the course of a procedure.

In another possible embodiment, an orifice connecting to the chamber may be located on the distal end so that an ice ball may be created or a cryogenic fluid may be sprayed from the distal end.

The apparatus of the present disclosure may be used to apply ultrasonic and cryogenic energy simultaneously and/or sequentially to ablate tissue. Simultaneous application of cryogenic and ultrasonic energy may be accomplished by providing cryogenic fluid to the distal end of the ultrasonic tip, activating the ultrasonic transducer, and then placing the distal end in contact with the tissue until the tissue is ablated.

Alternatively, the cryogenic energy and the ultrasonic energy may be applied sequentially by the apparatus to the tissue that is to be ablated. For example, a sequential application may begin by activating the ultrasonic transducer, placing the distal end of the ultrasonic tip in contact with the tissue, and then providing cryogenic fluid to the distal end. The sequence may be reversed, so that the sequence would begin by providing cryogenic fluid to the distal end, placing the distal end in contact with the tissue, and then activating the ultrasonic transducer. Various combinations of sequential and simultaneous applications of cryogenic and ultrasonic energy could be used during an ablation procedure, as would be recognized by those skilled in the art.

Cryogenic energy may be delivered to the tissue in different ways such as by providing cryogenic fluid to the ultrasonic tip and then placing the distal end in direct contact with the tissue. Alternatively, an ice ball on the distal end may be placed in contact with the tissue, or a cryogenic spray emanating from an orifice in the distal end of the ultrasonic tip may be used to deliver cryogenic energy to the tissue.

Combining ultrasonic energy with cryogenic energy can provide multiple benefits for the selective tissue removal process. One advantage of apparatus incorporating aspects of the present invention may be that adhesion of the ultrasonic tip to the tissue of the patient is avoided. Another advantage of apparatus incorporating aspects of the present invention may be that ultrasonic vibrations separate the tissue to be removed from healthy tissue. Another advantage of apparatus incorporating aspects of the present invention may be that high intensity ultrasonic energy alone may destroy the target tissue and merely be supplemented by the cryogenic effects. Another advantage of apparatus incorporating aspects of the present invention may be that ultrasonic energy makes the process less painful due to the pain relief effect resulting from the application of ultrasonic energy. Another advantage of apparatus incorporating aspects of the present invention may be that application of ultrasonic and cryogenic energy can have an antimicrobial effect on the treated and surrounding tissue. These and other novel aspects of the invention will become more apparent from the discussion and drawings below.

DETAILED DESCRIPTION OF THE INVENTION

The present invention relates to apparatus for ablation of tissues through a combination of ultrasonic and cryogenic energies and to methods of use of such apparatus. Highly controllable, precise delivery of ultrasonic and cryogenic energy simultaneously or in different sequences allows for the destruction of unwanted tissues without damaging surrounding tissue.

Figure 1:
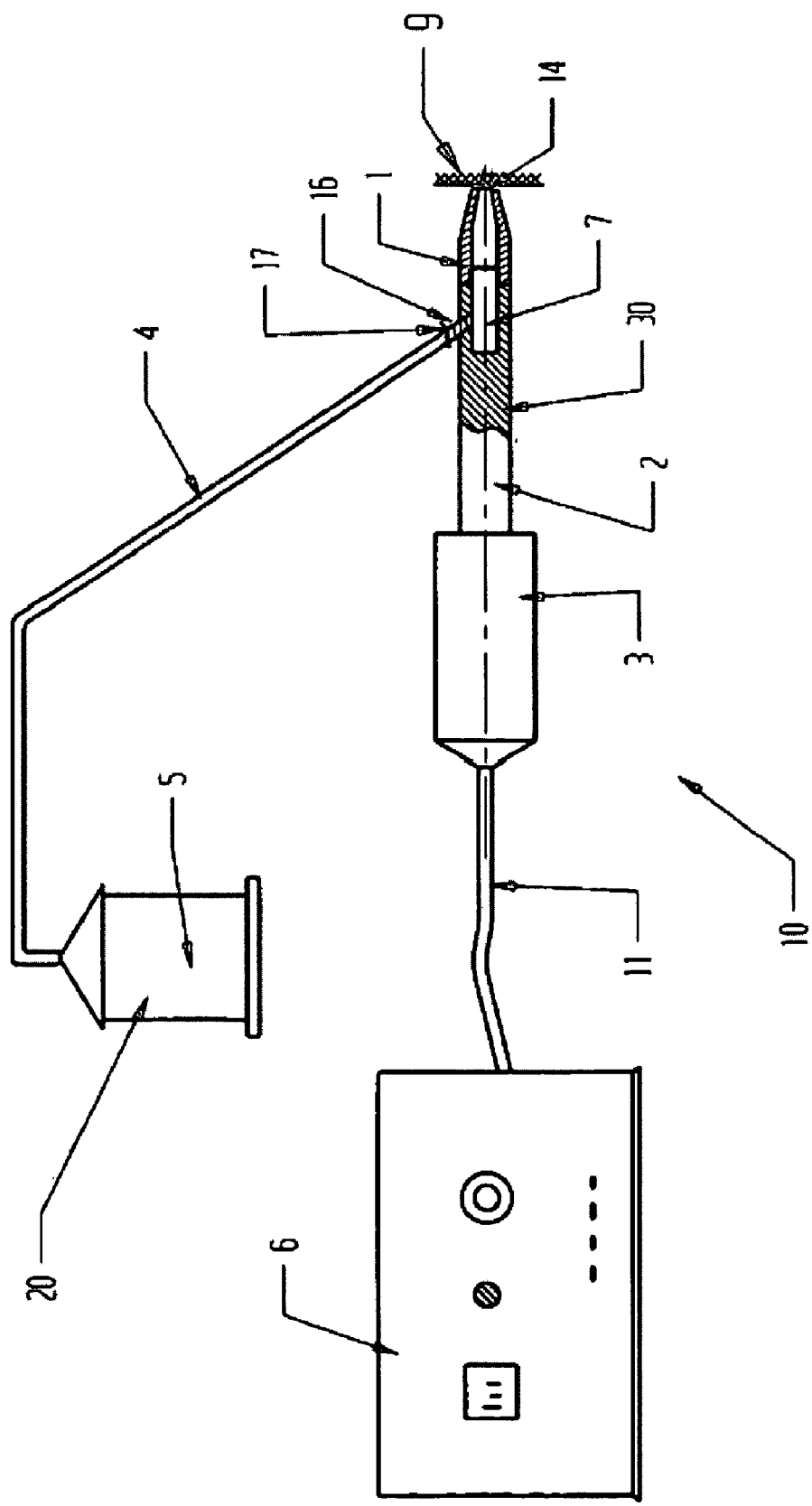
FIG. 1 is a general diagrammatic overview of an embodiment of a system for removal of tissues, which can provide a combination of ultrasonic and cryogenic energy.

A general view of an embodiment of the present apparatus 10 is shown in FIG. 1. The apparatus of the present invention 10 may be a hand-held device with a distal ultrasonic tip 1 that delivers ultrasonic and cryogenic energy in combination or in sequence to the skin tissue area 9 selected for treatment. The ultrasonic tip 1 is composed of a body, the body defining one or more interior chambers 7 for a cryogenic fluid 20. The cryogenic fluid 20 may be such gases or liquids as would be recognized by those skilled in the art such as, for example, liquid nitrogen. The cryogenic fluid 20 may be delivered to the interior chamber 7 from a source 5 through a cryogenic fluid delivery tube 4 which is attached to the ultrasonic tip 1 at the cryogenic fluid inlet tube 16. The cryogenic fluid inlet tube 16 defines an interior passage 17 connecting the cryogenic fluid delivery tube 4 to the one or more interior chambers 7. An ultrasonic transducer 3 may be connected to an ultrasound generator 6 by a cable 11. The ultrasonic tip 1 provides an ultrasonically active distal end 14 for delivering ultrasonic and cryogenic energy to the tissue 9 through direct contact, through ice ball 22, shown in FIG. 9, or through cryogenic spray 24, shown in FIG. 10.

The ultrasonic tip 1 is usually made from a metal such as titanium. The ultrasonic tip 1 may also be made from plastic and used disposably. The ultrasonic tip 1 may be excited by an ultrasonic transducer 3. The ultrasonic tip 1 may be connected to the ultrasonic transducer 3 through an ultrasonic horn 2.

Those skilled in the art will recognize that ultrasonic tip 1 comprises the ultrasonic horn 2, though it may be formed as two separate attachable pieces as depicted in FIG. 1. An ultrasonic transducer 3 is typically connected by cable 11 to an ultrasound generator 6. The ultrasonic transducer 3 may be operated at a frequency between 18 kHz and 100 MHz. The recommended operating frequency for the ultrasonic transducer is about 35 kHz. The ultrasonic transducer is pulsed according to a driving signal generated by the ultrasound generator 6 and transmitted to the ultrasonic transducer 3 by cable 11. The driving signals as a function of time may be rectangular, trapezoidal, sinusoidal, or other signal types as would be recognized by those skilled in the art. The ultrasonic frequency may be between 18 KHz and 20 MHz, or more. The preferable frequency is 20-60 KHz, and the recommended frequency is 35 KHz. The amplitude of the ultrasonic wave may be between 1 micron and 300 microns, or more. Preferably the amplitude of the ultrasonic wave is about 50 microns.

Figure 2:
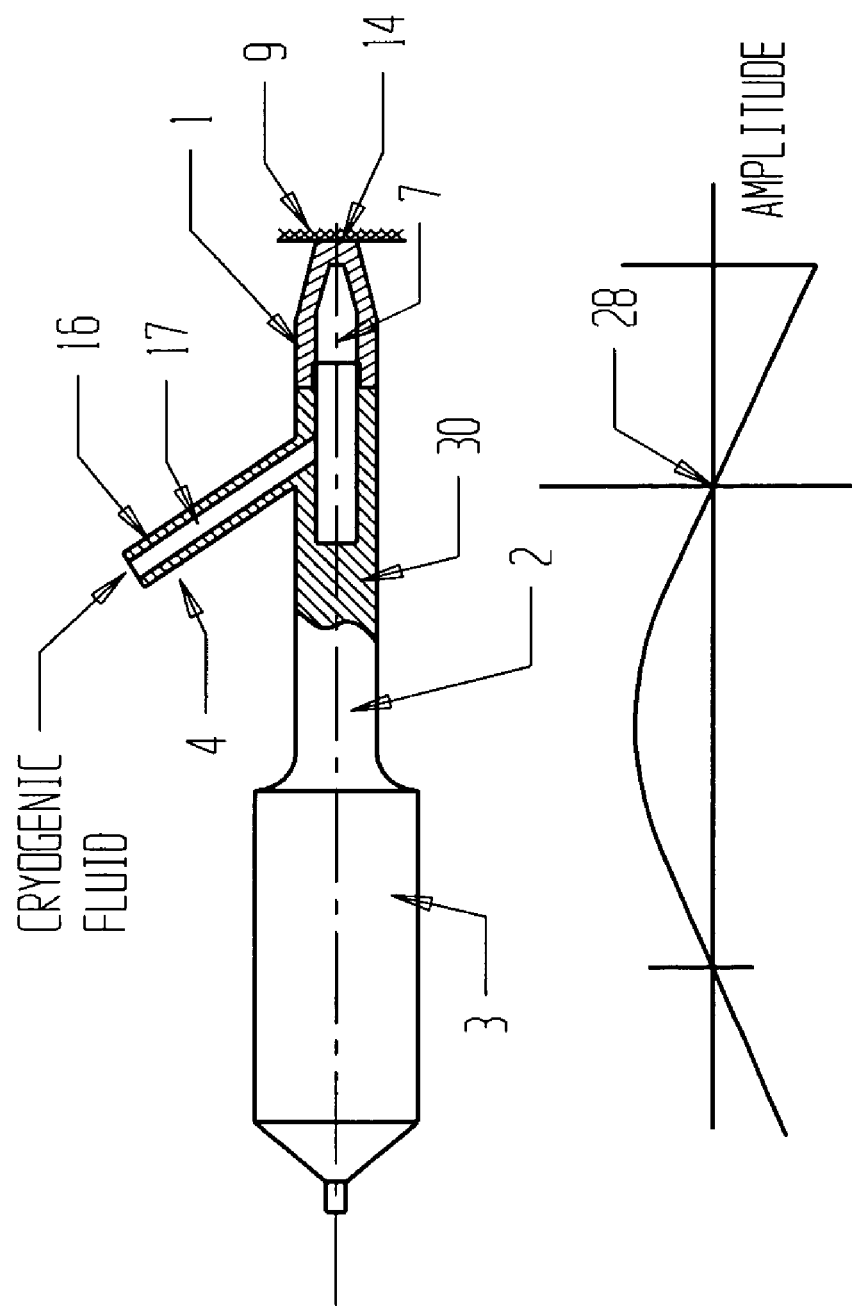
FIG. 2 illustrates an embodiment of an ultrasonic tip in accordance with the present invention configured to deliver cryogenic fluid from outside directly to the inside of the distal end portion of the tip and through one blunt orifice inside.

FIG. 2 is an illustration of ultrasonic transducer 3 with the interior passage 17 defined by the cryogenic fluid inlet tube 16 connected to the interior chamber 7 defined by the ultrasonic tip 1. A plot of the amplitude of the mechanical vibration of the ultrasonic horn 2 and ultrasonic tip 1 is also shown in FIG. 2. The inlet tube 16 is attached to the ultrasonic horn 2 or ultrasonic tip 1 at the mechanical resonance node 28, i.e., the point where the vibration amplitude of the ultrasonic horn 2 or ultrasonic tip 1 is zero. If tube 16 is not attached to the ultrasonic horn 2 or ultrasonic tip 1 at the resonance node 28, the intensity of the ultrasonic energy at the distal end 14 will be attenuated.

Figure 3:
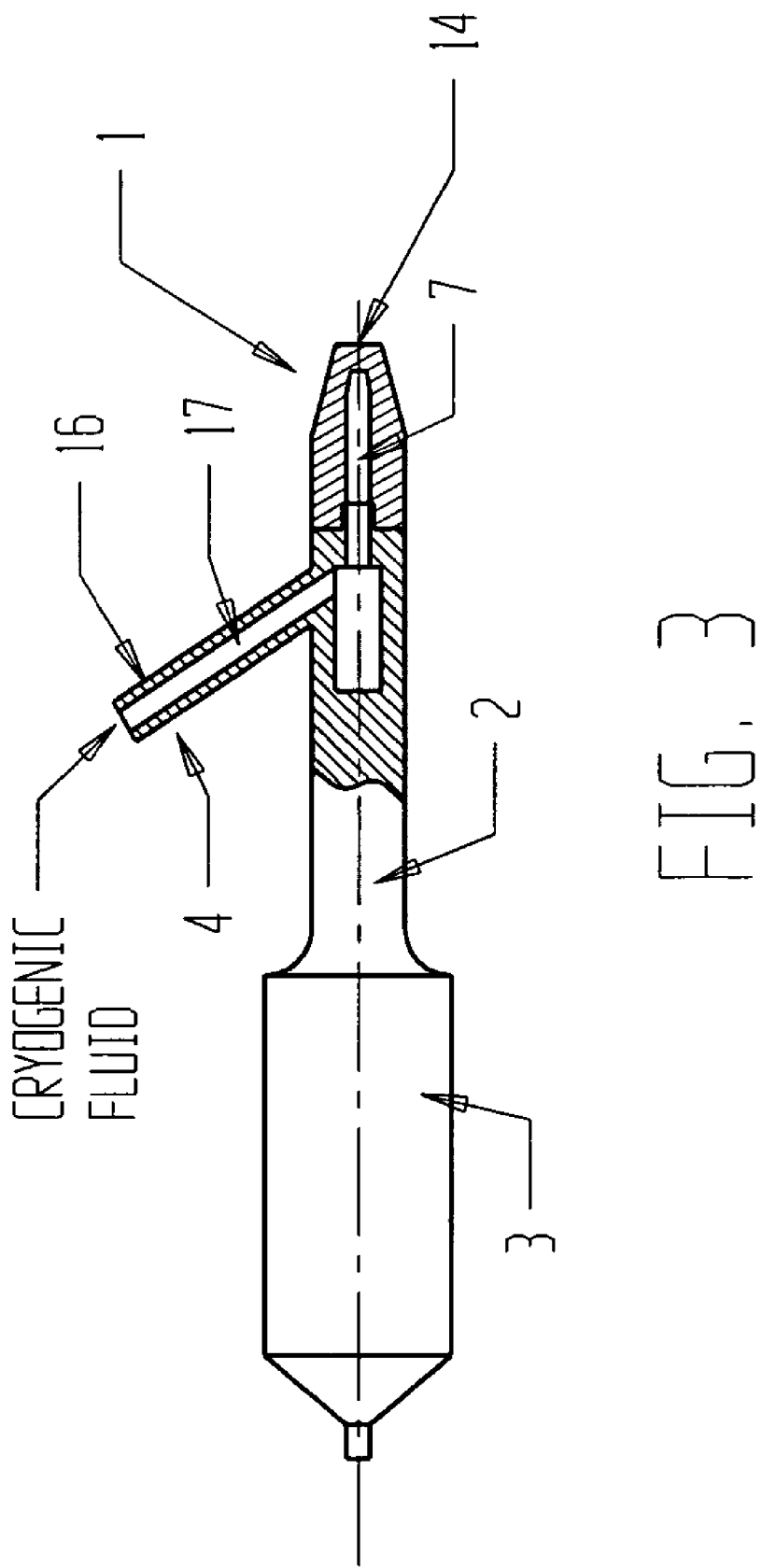
FIG. 3 illustrates an embodiment of an ultrasonic tip in accordance with the present invention configured to deliver cryogenic fluid through two blunt orifices inside.
Figure 10:
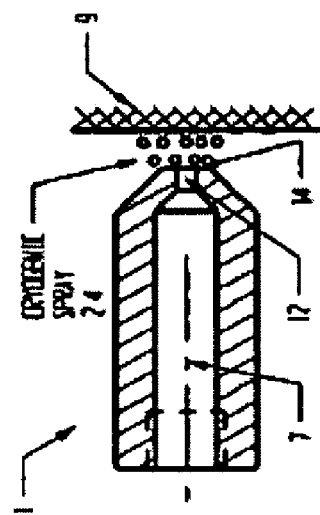
FIG. 10 illustrates an embodiment of the delivery of ultrasonic energy to the tissue through a cryogenic spray emitted toward the tissue from the radiation surface.
Figure 11:
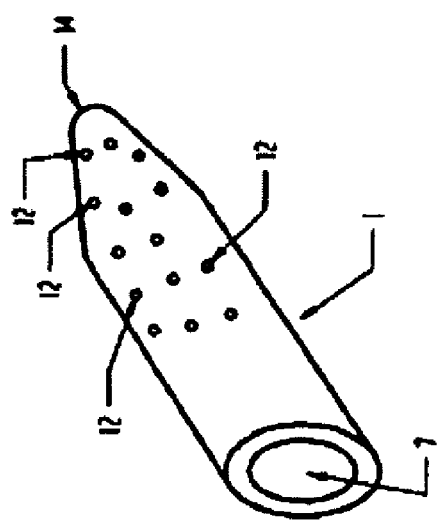
FIG. 11 illustrates a perspective view of an embodiment of the distal portion of an ultrasonic tip defining multiple orifices located on radial surfaces for tissue removal from the walls of body lumens (such as vessels, cavities, etc.)

FIG. 3 shows construction of the ultrasonic tip 1 with the delivery of cryogenic fluid through a chamber 7 having a narrow elongated portion extending toward the distal end 14. The number of chambers 7 must be at least one. In some embodiments, a plurality of chambers 7 may provide high efficacy of cryogenic ablation by increasing surface area. In other embodiments, a narrow elongated portion of a chamber 7 may direct cryogenic fluid to one or more orifices 12 on distal end radiation surface 14 (FIGS. 8, 9, and 10) or on the radial surface (FIG. 11).

Figure 4:
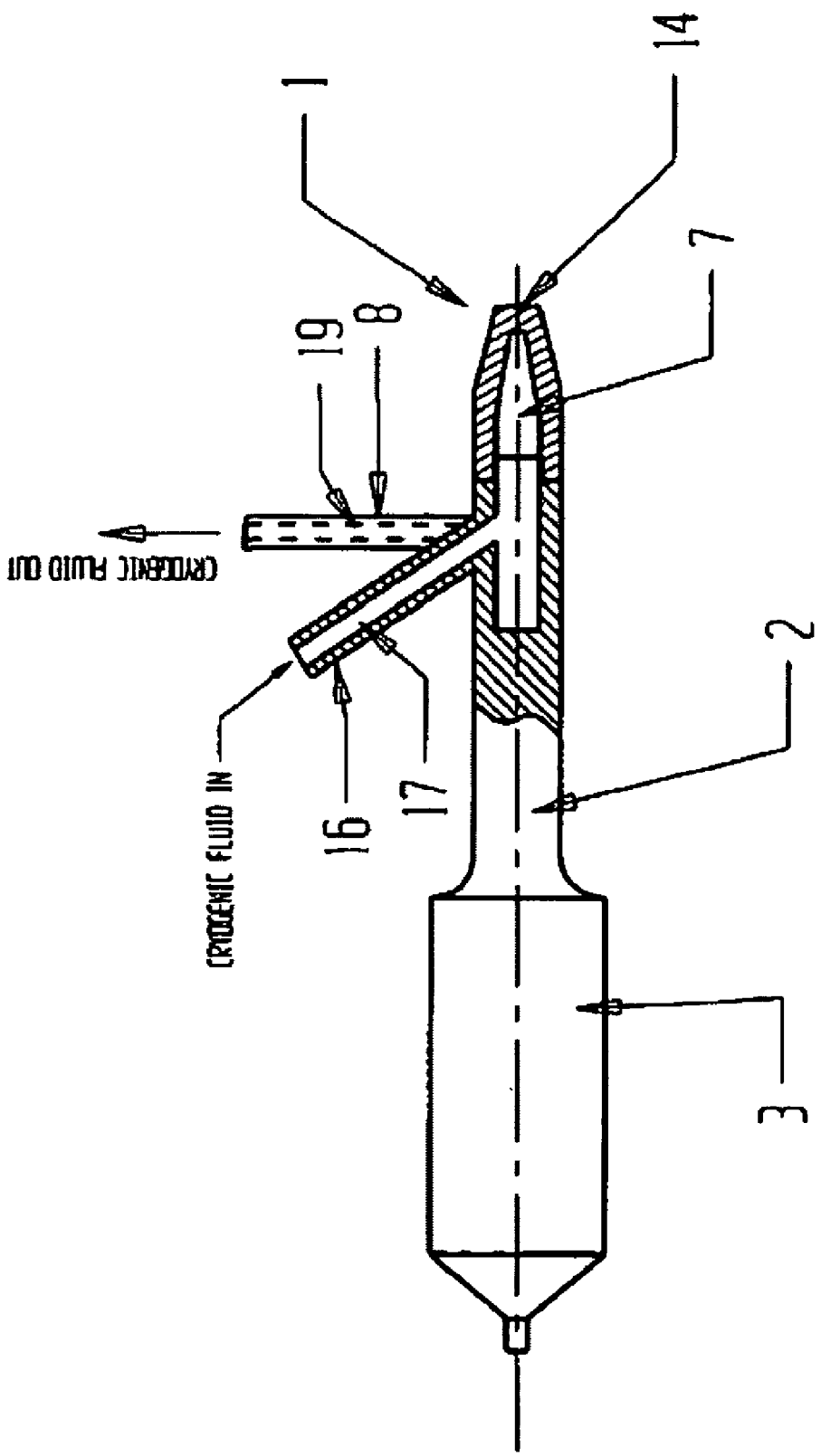
FIG. 4 illustrates an embodiment of an ultrasonic tip with two separate tubes from outside and two orifices inside for delivering cryogenic fluid in and out.

FIG. 4 illustrates an embodiment of an ultrasonic tip 1 having a cryogenic fluid inlet tube 16 that defines an interior passage 17 that connects the cryogenic fluid delivery tube 4 to the one or more interior chambers 7 and a cryogenic fluid outlet tube 8 that defines an interior passage 19 to the one or more interior chambers 7. Cryogenic fluid may then be added to the one or more interior chambers 7 through the cryogenic fluid inlet tube 16 and removed from the one or more interior chambers 7 through the cryogenic fluid outlet tube 8 so that the cryogenic fluid is circulated through the one or more chambers 7 of the ultrasonic tip 1.

Figure 5:
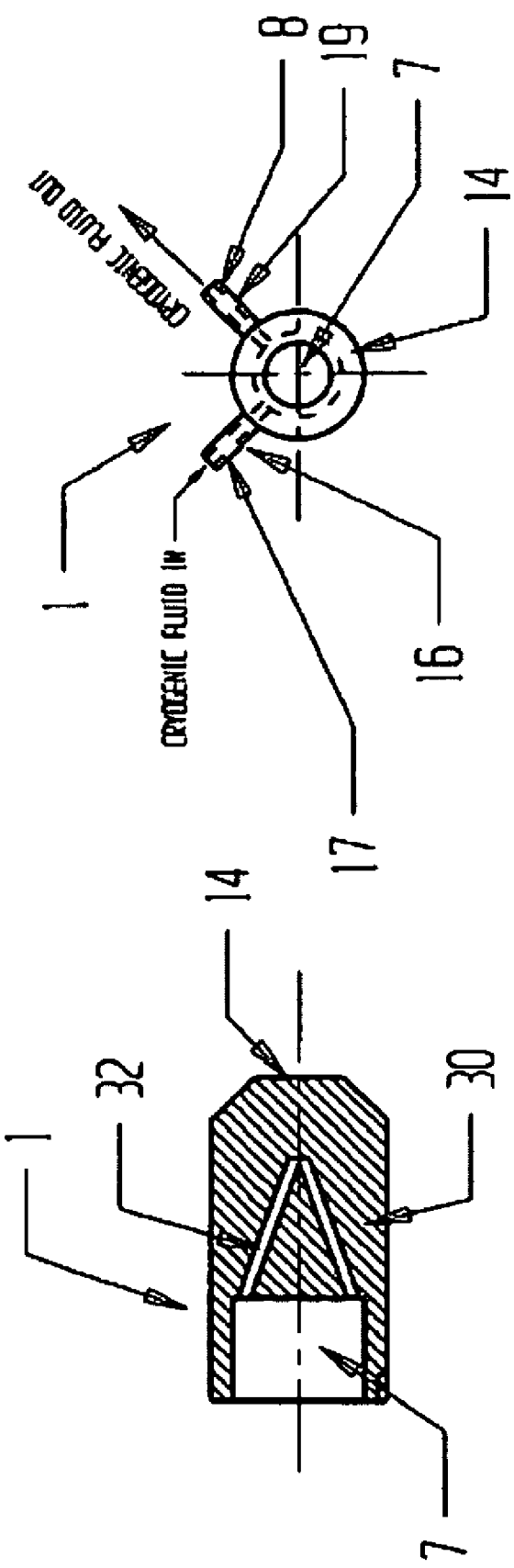
FIG. 5(a) illustrates a cross-sectional view of an embodiment of an ultrasonic tip comprising a channel extending through the distal portion of ultrasonic tip and in fluid communication with a chamber defined by the body of the ultrasonic tip.
FIG. 5(b) illustrates a horizontal cross-section of an embodiment of an ultrasonic tip with two orifices.

FIG. 5(a) is a side view of a chamber 7 defined by the body 30 of an ultrasonic tip 1. FIG. 5(a) also shows a channel 32 extending through the distal portion of ultrasonic tip 1 and in fluid communication with chamber 7 which may increase the efficiency of heat transfer between the ultrasonic tip 1 and cryogenic fluid. The channel 32 emanate from the chamber 7 toward the distal end 14 so as to allow cryogenic fluid to approach the distal end 14 while maintaining structural integrity of the body 30.

FIG. 5(b) shows a cross-section of an embodiment of an ultrasonic tip with two chambers 7 for improved circulation of a cryogenic fluid.

Figure 6:
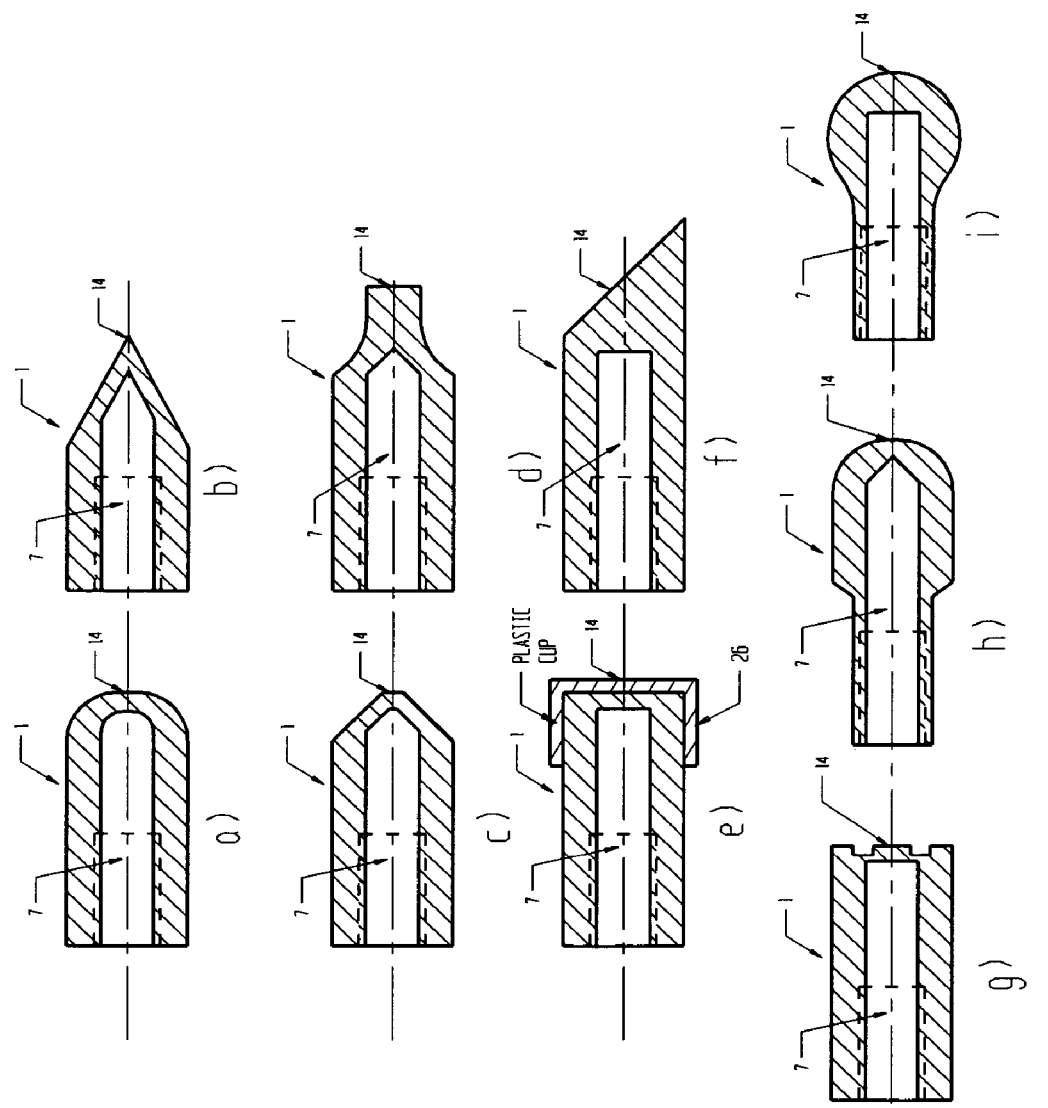
FIGS. 6(a) to 6(i) illustrate cross-sectional views of embodiments of different shapes of the distal end portion of an ultrasonic tip.

FIGS. 6(a) to 6(i) are cross-sectional views of different shapes of the distal end 14. FIG. 6(a) illustrates the rounded or oval distal end 14 which may be used for the ablation of larger regions of tissue 9. FIG. 6(b) illustrates a sharp cone distal end 14, which may be used for the precise ablation of smaller regions of tissue 9. FIGS. 6(c), 6(d), 6(e), and 6(f) illustrate various flat distal ends 14 for localized tissue 9 ablation. FIG. 6(g) shows a toothed distal end 14. A disposable plastic cover cap 26 that matches the geometrical form of the distal end 14 may be used to cover the distal end, as shown in FIG. 6(e).

The various geometric configurations for the ultrasonic tip 1 shown in FIGS. 6(h) and 6(i) are specially designed for the ablation of unwanted tissue layers in body lumen, such as vessels, cavities, etc. The ultrasonic tip is designed for insertion into body lumen without damage to the surrounding tissue.

Figure 7:
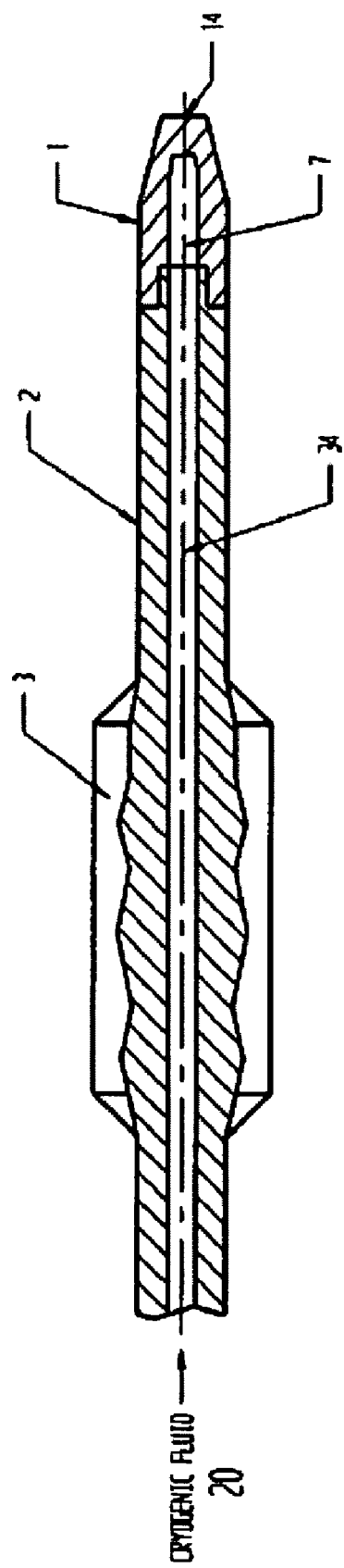
FIG. 7 illustrates an embodiment of the delivery of cryogenic fluid through an lumen that passes through the center of the ultrasonic transducer and through the horn as to form one or more chambers defined by the body of the ultrasonic tip.

FIG. 7 illustrates the delivery of cryogenic fluid 20 through a lumen 34 that passes through the center of ultrasonic transducer 3 and through ultrasonic horn 2 as to form one or more chambers defined by the body 30 of the ultrasonic tip. This particular embodiment may offer manufacturing advantages as will be recognized by those skilled in the art upon review of the present disclosure.

Figure 8:
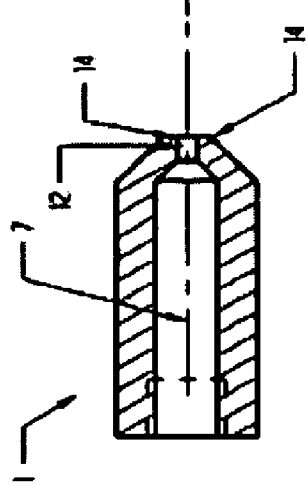
FIG. 8 illustrates a cross-sectional view of an embodiment of an ultrasonic tip with the interior chamber communicating with an orifice to a radiation surface.
Figure 9:
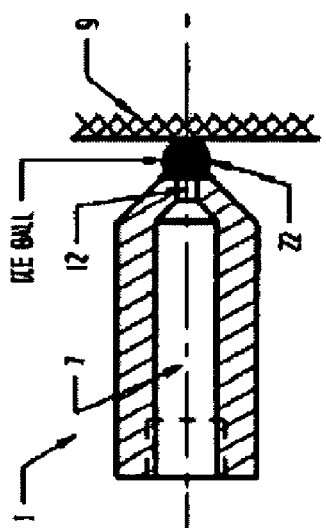
FIG. 9 illustrates an embodiment of the delivery of cryogenic and ultrasonic energy to the tissue through an ice ball positioned between radiation surface and tissue.

FIG. 8 illustrates a cross-sectional view of an ultrasonic tip 1 having an orifice 12 between the chamber 7 and the distal end 14 so that cryogenic fluid 20 may flow from the chamber 7 through the orifice 12 so as to emanate from the distal end 14. This type of embodiment allows the creation of an ice ball 22 on the distal end 14, as shown in FIG. 9, and/or cryogenic spray shown in FIG. 10. Cryogenic and ultrasonic energy can then be delivered to the tissue 9 through ice ball 22 and/or cryogenic spray between distal end 14 and tissue 9.

FIG. 11 presents a three-dimensional view of an ultrasonic tip 1 with the multiple orifices 12 located on the distal end 14 for ablation of tissue on body lumen walls and sidewalls (such as, vessel, cavities, etc.) in perimeter.

Figure 12:
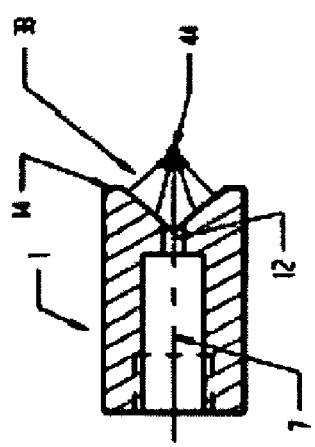
FIG. 12 illustrates an embodiment of an ultrasonic tip having a reverse cone shaped radiation surface for focusing ultrasonic energy to the tissue.
Figure 13:
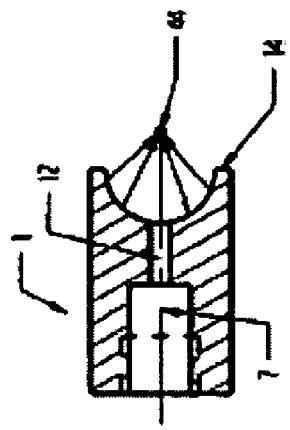
FIG. 13 illustrates an embodiment of an ultrasonic tip having a concave shaped radiation surface for focusing ultrasonic energy to the tissue.

FIG. 12 shows the backward cone shape for a distal end 14 that focuses ultrasonic energy on a focal point 44 and FIG. 13 shows the concave shape for a distal end 14 that focuses ultrasonic energy on a focal point 44.

An apparatus according to the present invention may be used for the selective ablation of unwanted skin tissue such as warts, moles, pre-cancerous skin growths, tumors, melanomas, and scars. In one exemplary technique for using the apparatus, the cryogenic and ultrasonic energy are applied simultaneously to the tissue that is to be ablated. This technique includes providing cryogenic fluid 20 to the distal end 14, activating the ultrasonic transducer 3, and then placing the distal end 14 either proximate to and/or in contact with the tissue 9 until the tissue is ablated.

Alternatively, the cryogenic energy and the ultrasonic energy may be applied sequentially by the apparatus to the tissue that is to be ablated. For example, sequential application may begin by activating the ultrasonic transducer 3, placing the distal end 14 proximate to and/or in contact with the tissue 9, and then providing cryogenic fluid to the distal end 14. The sequence may be reversed, in which case the sequence would begin by providing cryogenic fluid 20 to the distal end 14, placing the distal end 14 proximate to and/or in contact with the tissue 9, and then activating the ultrasonic transducer. Combinations of sequential applications of cryogenic and ultrasonic energy and the simultaneous application of cryogenic and ultrasonic energy may be used in combination with the sequential application of cryogenic and ultrasonic energy during ablation of tissue 9 as would be recognized by those skilled in the art.

Cryogenic energy may be delivered to the tissue by providing cryogenic fluid 20 to the distal end 14 and placing the distal end proximate to the tissue and/or placing the distal end in contact with the tissue 9. Alternatively, an ice ball 22 on the distal end 14 may be placed in contact with the tissue, or cryogenic spray 24 from an orifice 12 in the distal end 14 may be used to deliver cryogenic energy to the tissue.

Although specific embodiments and methods of use have been illustrated and described herein, it will be appreciated by those of ordinary skill in the art that any arrangement that is calculated to achieve the same purpose may be substituted for the specific embodiments and methods shown. It is to be understood that the above description is intended to be illustrative and not restrictive. Combinations of the above embodiments and other embodiments as well as combinations of the above methods of use and other methods of use will be apparent to those having skill in the art upon review of the present disclosure. The scope of the present invention should be determined with reference to the appended claims, along with the full scope of equivalents to which such claims are entitled.

I claim:

1. An apparatus comprising:
   a. an ultrasound tip, comprising:
      i. a body defining a chamber;
      ii. a tube in communication with the chamber;
      iii. a distal end;
      iv. one or a plurality of orifices connected to the chamber in the distal end; and
      v. an ice ball, that is separate and distinct from the tissue selected for treatment, on the distal end of the ultrasound tip through which ultrasonic energy is delivered to the tissue; and
   b. an ultrasonic transducer connected to the ultrasound tip through an ultrasound horn.

2. The apparatus of claim 1, wherein the ultrasonic transducer operates at a frequency between 18 KHz and 60 MHz.

3. The apparatus of claim 1, wherein the ultrasonic transducer operates at a frequency between 20 KHz and 100 KHz.

4. The apparatus of claim 1, wherein the ultrasonic transducers operates at about a 35 KHz frequency.

5. The apparatus of claim 1, wherein the amplitude of the ultrasonic wave is between 1 micron and 300 microns.

6. The apparatus of claim 1, wherein the amplitude of the ultrasonic wave is about 50 microns.

7. The apparatus of claim 1, wherein the distal end is rounded.

8. The apparatus of claim 1, wherein the distal end is flat.

9. The apparatus of claim 1, wherein the distal end is a sharp cone.

10. The apparatus of claim 1, wherein the ultrasound tip's distal end has a sharp edge.

11. The apparatus of claim 1, wherein the ultrasound tip's distal end has a toothed edge.

12. The apparatus of claim 1, wherein the ultrasound tip's distal end is concave.

13. The apparatus of claim 1, further comprising a lumen passing through the center of the ultrasonic transducer.

14. A method for removing tissue from a patient, comprising:
   a. providing an ultrasonic transducer having an ultrasonic tip, comprising:
      i. a body defining a chamber;
      ii. a tube in communication with the chamber;
      iii. a distal end;
      iv. one or a plurality of orifices connected to the chamber in the distal end; and
      v. an ice ball, that is separate and distinct from the tissue, on the distal end of the ultrasonic tip;
   b. delivering a cryogenic fluid into the chamber of the ultrasonic tip through the tube in communication with the chamber;
   c. delivering cryogenic energy from the ultrasonic tip to the tissue through the ice ball on the distal end of the ultrasonic tip;
   d. exciting the ultrasonic tip; and
   e. delivering ultrasonic energy from the ultrasonic tip to the tissue through the ice ball on the distal end of the ultrasonic tip.

* * * * *